United States Patent [19]

Dunfield et al.

[11] Patent Number: 4,888,983
[45] Date of Patent: Dec. 26, 1989

[54] PROFILOMETRY

[75] Inventors: Lawrence G. Dunfield, Bright's Grove; Kar P. Lok, Sarnia, both of Canada

[73] Assignee: BASF Aktiengesellschaft, Ludwigshafen, Fed. Rep. of Germany

[21] Appl. No.: 183,933

[22] Filed: Apr. 20, 1988

[51] Int. Cl.$^4$ ............................................. G01N 33/34
[52] U.S. Cl. ......................................... 73/104; 73/105; 356/448
[58] Field of Search ............. 73/105, 104, 159, 150 R; 356/448

[56] References Cited

U.S. PATENT DOCUMENTS

| | | | |
|---|---|---|---|
| 3,846,027 | 11/1974 | Hyman et al. | 356/448 X |
| 3,936,665 | 2/1976 | Donoghue | 162/252 X |
| 3,970,393 | 7/1976 | Krygeris et al. | 356/448 X |
| 3,999,864 | 12/1976 | Mutter | 356/448 |
| 4,072,426 | 2/1978 | Horn | 356/448 |
| 4,124,803 | 11/1978 | Bowers | 356/448 X |
| 4,149,187 | 4/1979 | Palmer et al. | 73/105 X |
| 4,178,095 | 12/1979 | Champion et al. | 356/448 X |
| 4,300,981 | 11/1981 | Carstens | 162/132 X |
| 4,476,489 | 10/1984 | Weltlich et al. | 73/105 X |
| 4,541,273 | 9/1985 | Berg | 73/159 X |
| 4,566,798 | 1/1986 | Haas | 356/448 |
| 4,574,625 | 3/1986 | Olasz et al. | 73/105 |
| 4,580,438 | 4/1986 | Horand | 73/150 R X |

OTHER PUBLICATIONS

W. Roehr, "Effect of Smoothness and Compressibility on the Printing Quality of Coated Paper", 11/1955, TAPPI vol. 38, No. 11, pp. 660-664.

H. J. Kent et al., "Applications on Novcel Techniques for Quantitative Characteristics of Coating Structure" 1986, TAPPI Proceedings pp. 103-112.

P. Aschan et al., "Broad Surface Structure and Gravure Printability", 1984, TAPPI Proceedings, pp. 149-155.

H. J. Kent, "Factors Influencing the Printability of LWC Papers" English China Clays, pp. 2-7, Pub. by Apr. 1988.

Sultronic 3P-Total Portability in Surface Measurement; p. 10, Product Brochure; Pub. by Apr. 1988.

Primary Examiner—Tom Noland
Attorney, Agent, or Firm—Bruce E. Harang

[57] ABSTRACT

The properties, and particularly the print gloss, of coated, unprinted paper may be predicted using surface profilometry. The profilometer is preferably hand held so the contour of paper in jumbo rolls in the finishing and storage area may be determined quickly. The surface contour is then compared to a calibration curve to predict the desired property.

7 Claims, 4 Drawing Sheets

PROFILOMETRY

FIELD OF THE INVENTION

The present invention relates to the measurement of the properties of coated paper. More particularly the present invention relates to the measurement of the surface contour of paper and optionally relating that measurement to a number of properties of paper including the print properties of the coated paper, particularly print gloss.

BACKGROUND OF THE INVENTION

There is a thrust in industry to produce high quality products consistently. This is also the case in the paper industry. Particularly, the paper industry is concerned with the print properties of paper. The coated paper industry faces several major problems in determining these print properties. The printing of paper usually takes place remote from the mill. Generally large quantities of paper have been prepared before the paper is actually commercially printed. To try to minimize these problems a series of laboratory tests have been developed to measure the print properties of paper including print gloss. Unfortunately, the most accurate test is to condition a sample of paper (usually overnight), print it, and then test it. Paper mills run at speeds of about 1500 m/min. Even if the testing could be completed in 1 or 2 hours there is a potential to produce huge amounts of poor quality material. There is a need to develop a simple, low cost, portable test which will relatively quickly indicate the potential print gloss of coated paper. Due to the high speed of the paper web it is not anticipated that the type of profilometer used in the present invention could be used continuously on the paper coater.

A method to test the surface smoothness of paper does exist but it is not portable, and it is expensive. The currently accepted method in North America is the Parker Surface Roughness Test (Print Surf) method. This method measures the air which passes between the surface of a coated paper and a flat surface of either steel or rubber. The apparatus to carry out such a test costs about $20,000 (CDN.). The equipment is not portable and requires laboratory staff and space. More importantly the test lacks a high resolution for the smoothest surfaces. The present invention uses a hand held portable device which has high resolution and costs about $4,000 (CDN.).

Portability is important from a production point of view as it provides immediate information. For example, the present invention contemplates that the surface profile of paper in jumbo rolls in the finishing area could be measured in the storage area. The read out of the profilometer is immediate and may be related to a number of properties including predicted print gloss.

Some initial work in this area was done by Kimberly-Clark Corp. in the early 1950's. This work was presented in "Effects of Smoothness and Compressibility on the Printing Quality of Coated Paper" Walter W. Rocher TAPPI Vol. 38 No. 11 November 1955 pg. 660. The paper does not seem to contemplate or suggest relating the measurements taken to print gloss or other properties of the paper. Additionally, the device used does not appear to be portable or hand held.

There has been some work on characterizing paper using profilometry. One of the current leaders in this field is English China Clays International which uses a modified, non-portable, Talystep (trade mark) profilometer instrument. The data is analysed using Fourier transforms to segregate different types of periodic occurrences. These then may be attributed to macroroughness (e.g. the roughness of the base sheet) and microroughness (e.g. the roughness of the coating). The data may also be used to generate computer plots of the surface topography of coated paper. ("Applications of Novel Techniques for Quantitative Characterisation of Coating Structure" H. J. Kent et al TAPPI 1986 Coating Conference pg. 103)

A paper presented at the TAPPI 1984 Coating Conference (pg. 149) "Board Surface Structure and Gravure Printability" Per-Johan Aschan Tapio Makkonen and Jorma Paakko, the Finnish Pulp and Paper Institute, discusses the use of profilometry to classify the cumulative number of voids of a specified size which occur during a profile measurement (CN number) and their distribution (Sd). These data together with the Parker Surface Roughness for the base uncoated sheet have been correlated to the Heliostat print test values for printed board. In the paper it is proposed to predict the Helio test value as a function of both base board and coated surface smoothness. E.g. Helio=$589.8-0.103$ CN$-99.2$ BPPS$-258.0$ Sd$+49.2$ Sd.BPPS in which CN is the cumulative number of voids, BPPS is the base board smoothness (Parker Surface Roughness) and Sd is the distribution index for voids. Both CN and Sd are determined using a profilometer. The data suggest that profilometry is useful provided the base board surface smoothness is consistent (e.g. different curves for different base boards). The paper suggests that poor correlation is achieved using a representative range of papers and a profilometry device. The profilometry device used was built by the Finnish Pulp and Paper Research Institute and it appears that the device is not portable as the data is generated using lab samples two meters in length.

The present invention seeks to provide a rapid method to measure the surface profile of paper and relate this measurement to other properties of the paper and the printed paper using a portable (hand held) profilometer.

SUMMARY OF THE INVENTION

The present invention provides a rapid method to determine surface properties of coated paper, and where required predict the printed properties of coated paper which comprises taking one or more measurements across the surface of an unprinted coated paper using a portable profilometer comprising a stylus, a traverse unit, a pick up, and one or more members selected from the group consisting of a recorder, a calculator, a display unit, and a computer interface means, to measure the surface contour of the paper in a direction perpendicular to the plane of the paper within the range ±500 micrometers from the mean surface of the paper, and where required one or more surface characterizations of the unprinted coated paper selected from the group consisting of specular gloss, reflectance and air resistance; and relating the measured values to similar measured values of a representative sample of papers in a generally recognized category of the paper industry for which the surface properties and printed properties of sample paper have been measured.

DETAILED DESCRIPTION

Figure 1:
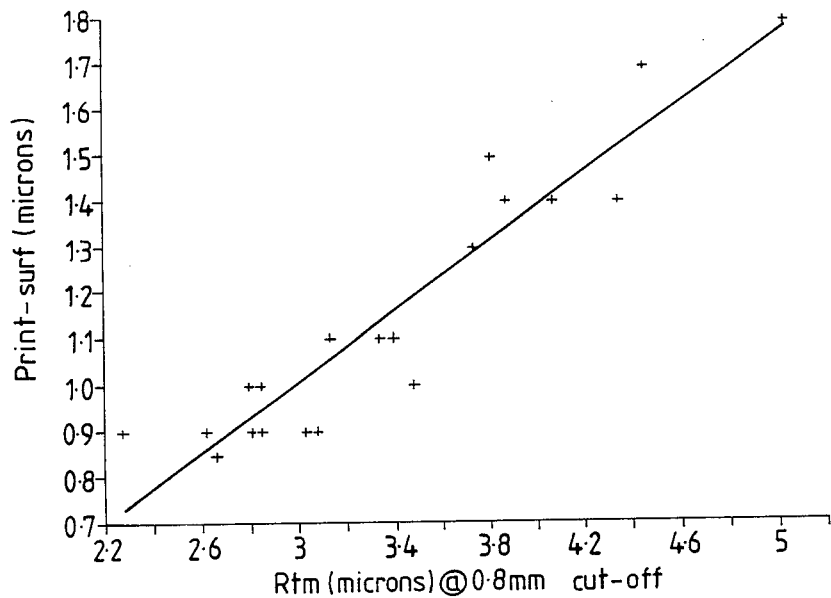
FIGS. 1-6 are curves derived from surface contour measurement data having respective correlation coefficients of 0.94, 0.74, 0.71, 0.81, 0.823, and 0.67 plotting conventional surface characterization data against profilometry data, and a plot of measured print gloss against a print gloss calculated from a two variable equation derived from regression analysis of data.

FIG. 1 is a plot of Parker Surface Roughness versus mean profile (e.g. the average peak to valley height—Rtm (RzDIN$_{4768}$)).

Figure 2:
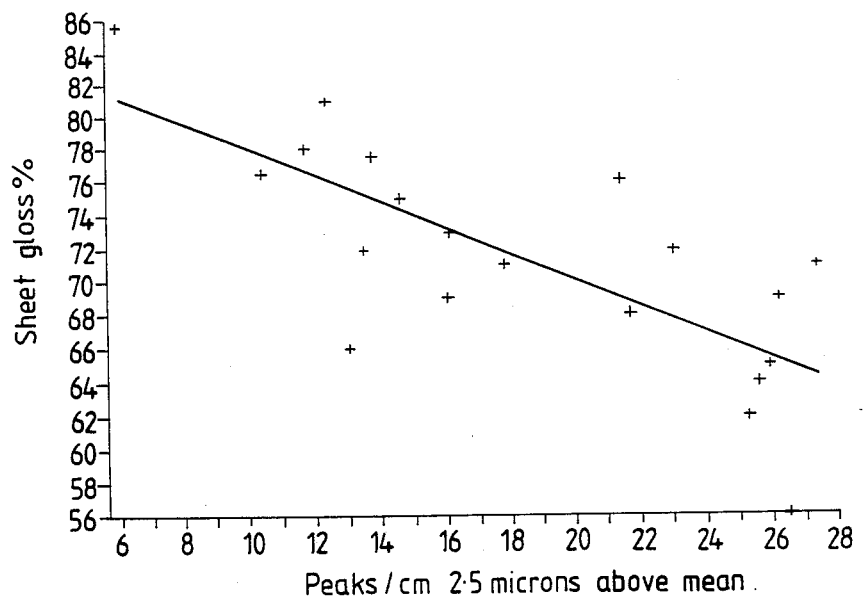

FIG. 2 is a plot of Sheet Gloss versus Peak count (Pc) (e.g. per cm 2.5 micrometers above mean surface). As used in this specification peak count means the number of peaks per cm a specified distance above the mean surface and means the number of times during the traverse of one cm. of the surface that the tip of a stylus rises at least the specified distance above the mean surface and falls at least the specified distance below the mean surface. Typically the specified distance is 2.5 micrometers. To have one count on the peak count the tip of the stylus must rise 2.5 micrometers above the mean surface and then fall 2.5 micrometers below the mean surface.

Figure 3:
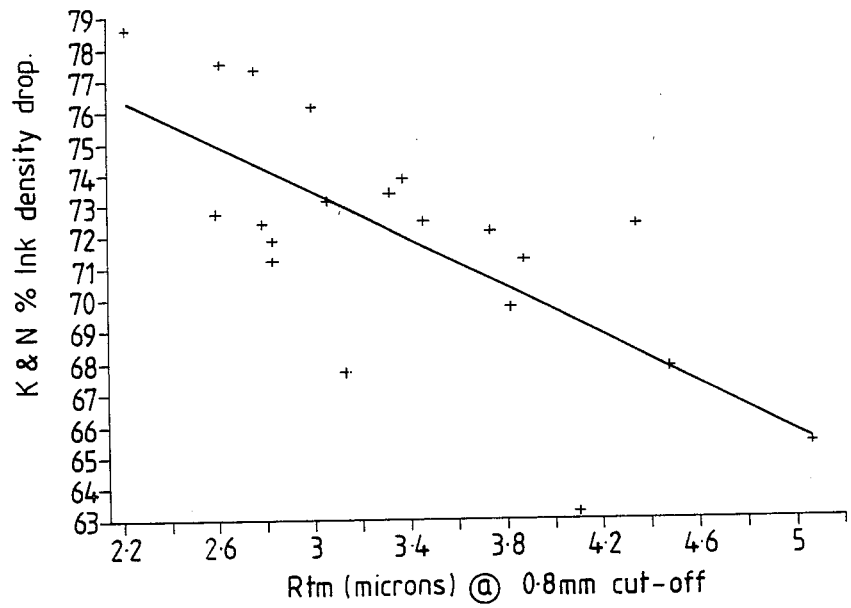

FIG. 3 is a plot of K and N percentage Ink Density Drop versus Rtm.

Figure 4:
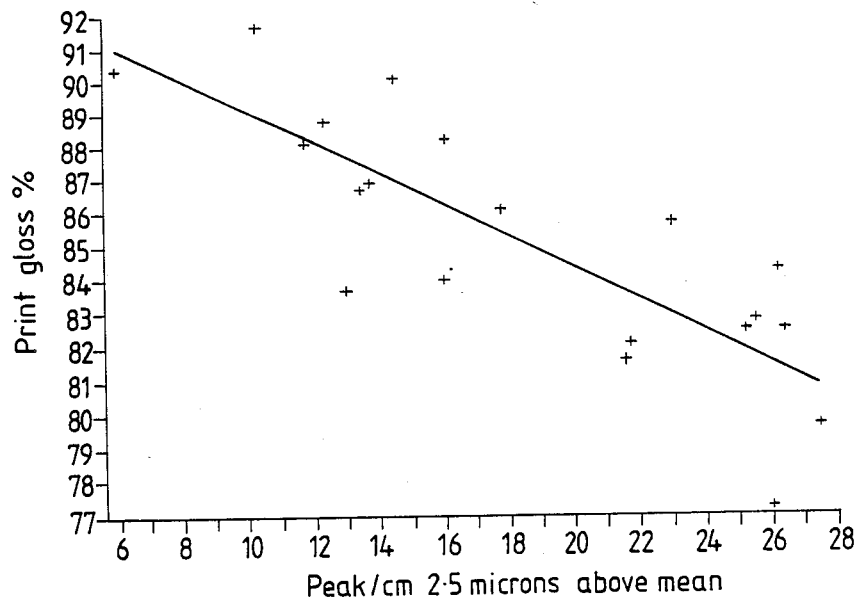

FIG. 4 is a plot of Print Gloss versus Peak count per cm 2.5 micrometers above mean surface.

Figure 5:
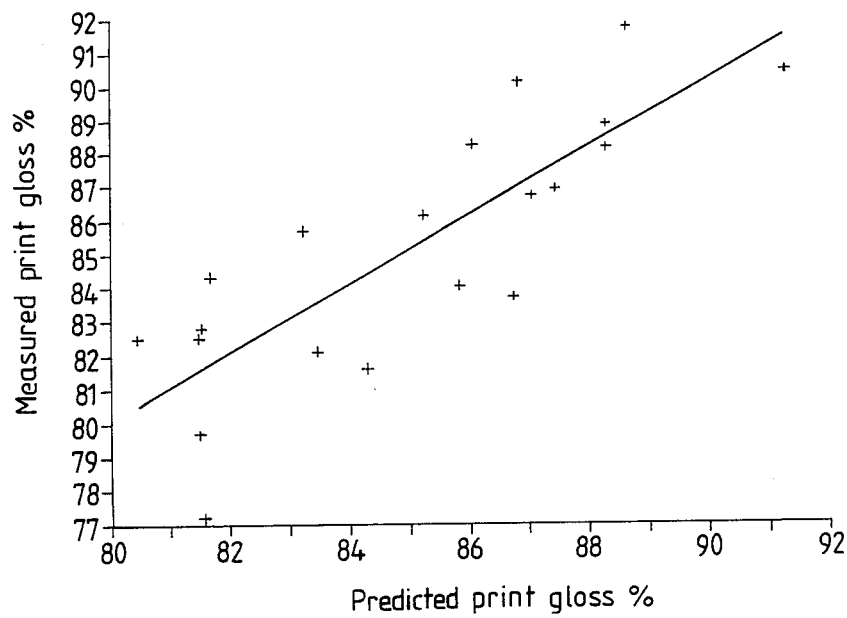

FIG. 5 is a plot of Measured Print Gloss versus Predicted Print Gloss.

Figure 6:
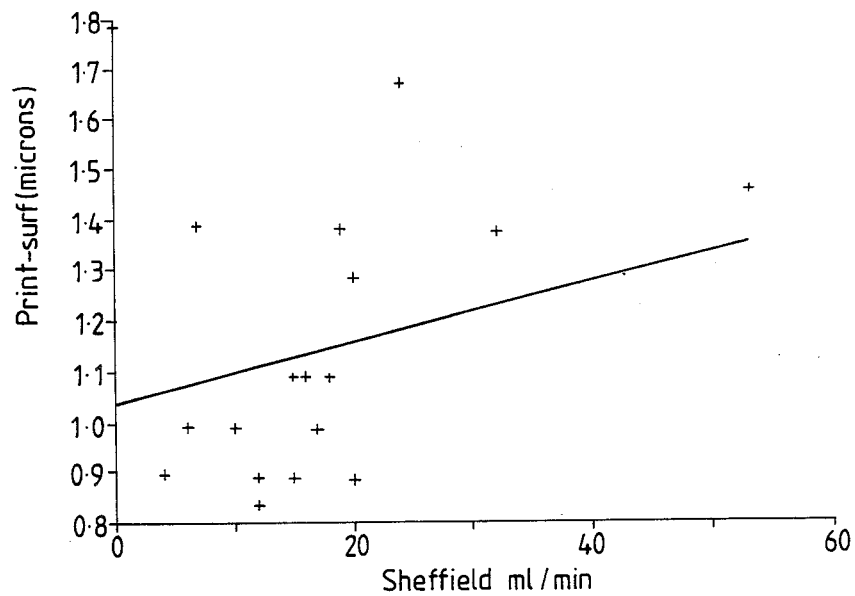

FIG. 6 is a plot of Parker Surface Roughness versus Sheffield Smoothness.

Figure 7:
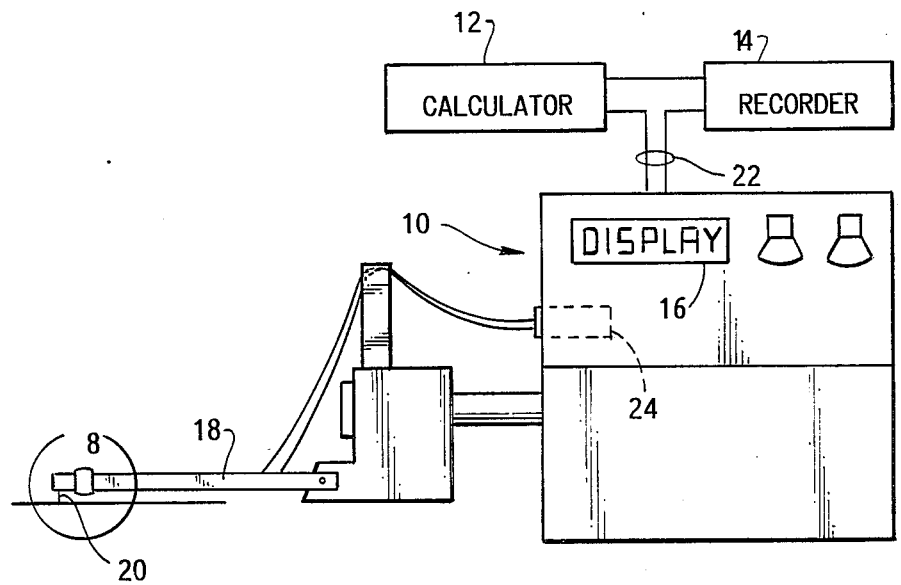
FIG. 7 is a schematic representation of a prior art commercially available portable profilometer useful in Applicants' invention with programming in accordance with Applicants' invention.
Figure 8:
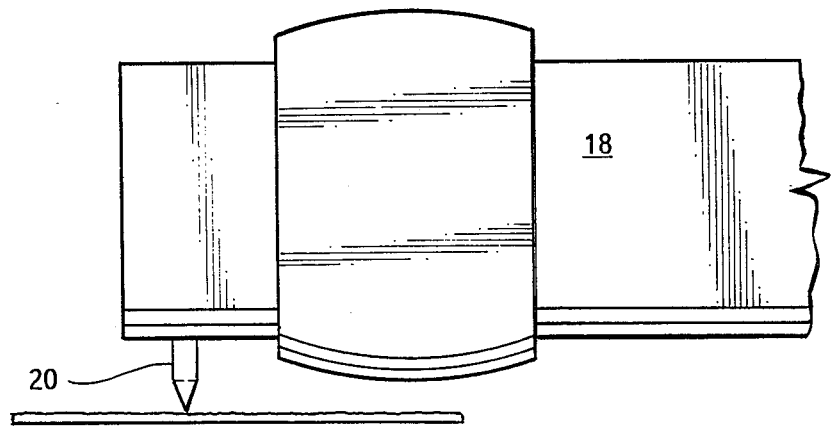
FIG. 8 is a detailed view of the end of a known prior art traverse arm incorporated in the known profilometer of FIG. 7.

FIG. 7 is a schematic representation of a prior art portable profilometer useful with programming in accordance with the invention to produce applicants' invention FIG. 8 is a enlarged schematic of one end of the traverse arm of FIG. 7.

Profilometers useful in accordance with the present invention are portable. Preferably they are hand held. A particularly useful device is marketed by Taylor-Hobson under the trade mark SURTRONIC 3P. Taylor-Hobson trade literature discloses the instrument is particularly useful to measure machined metal parts. The literature does not suggest the device would be useful in characterizing the smoothness of coated paper and predicting the surface and print properties of the paper.

The profilometer (10) comprises a stylus (20), a traverse unit (8) and a pick up (24). The stylus should be a very fine pointed stylus. Preferably the stylus will be diamond with a tip radius not greater than 10 micrometers, most preferably less than or equal to 5 micrometers. Preferably the stylus is used in conjunction with a biased holder to press the stylus against the plane of the paper or the paper surface. The stylus should be capable of moving in a direction perpendicular to the plane of the paper up to a maximum of ±500 microns. Preferably the movement will be considerably less than 500 microns, preferably it will be less than ±100, most preferably up to ±10 microns from the mean surface of the paper.

The traverse will preferably be a powered traverse. The traverse will comprise an arm upon which the stylus is mounted. Preferably the arm is drawn in a linear direction, rather than sweeping out an arc, across the paper surface. Preferably the arm has an extension up to about 200 mm, most preferably about 185 mm. The arm is then drawn into the device at a controlled fixed rate usually about 0.25 to 1.0 mm/sec. The actual traverse distance (e.g. stroke) need not be the entire length of the arm of the traverse unit. The distance of travel may be in the range 1.5 to 25 mm. It is preferred that the actual measurement be made over a portion of the stroke, for example in the range from 0.2 to 2.5 mm. There may be several distances within a traverse over which measurements may be taken such as 0.25, 0.8 and 2.5 mm. Thus one traverse may generate multiple measurements. The distance over which measurements are taken is sometimes referred to as "cut off".

The stylus movement perpendicular to the plane of the surface of the paper is measured by a pick up. Preferably the pick up is a (magnetic) reluctance pick up outputting an electrical signal. The electrical signal may be fed into a recorder (14) or calculator (12), or the signal may sequentially travel through both a recorder (14) and calculator (12). Preferably the recorder can be combined or replaced with a computer interface (22) so that cut offs other than 0.2 to 2.5 mm may be employed and so that the signals may be subjected to various mathematical analysis, such as regression analysis. The recorder or recorder/calculator or the computer if a computer interface (e.g. jack) is used should have a print out or a display (16). The calculator or computer should be pre-programmed or programmable. This also makes it possible to analyse the data over different cut offs and to determine what is the significance of various parameters and what are significant variations in the parameter. Some of the data which are useful include:
(i) mean profile (e.g. the average of peaks and valleys (Rpm);
(ii) maximum height of the profile (Rp);
(iii) maximum peak to valley height;
(iv) mean peak height; and
(v) Peak count (Pc) a count of the number of peaks per cm above the mean surface by a specified height (e.g. peaks a specified appropriate variable such as 2.5 micrometers above mean surface height or as a percentage (e.g. number of peaks per cm within 15% of maximum peak height).

To relate the surface profile to the surface or print properties of the paper a representative sample of papers generally recognized as being within the same class, such as enamel offset papers, light coat weight offset papers, light coat weight gravure papers, etc. are selected. Generally the larger the sample the more accurate the relation. Preferably the sample size should be no less than 9, preferably greater than 16 sheets of paper. The surface characteristics of the sample papers are then determined using a profilometer. Usually this should be done by taking the average of a number of measurements for each paper (e.g. usually at least 5 measurements). Then the specific properties of the paper are measured using standard paper measurements (e.g. TAPPI) such as Parker Surface Roughness (Print Surf), Gloss, K and N percentage Ink Density Drop, and Print Gloss. The measurements taken with the profilometer may be plotted on one axis (usually x) and a set of data from current surface characterization techniques are plotted on the other axis (usually y). This will generate a calibration curve. In the alternative, if desired the profilometry data optionally together with the current surface characterization such as specular gloss (preferably taken at 75°), reflectance, and air resistance (porosity) data may be mathematically regressed and plotted or calculated as a function. The regression may generate two types of equations (e.g. Dunfield equations) of the form:

(i) Surface or print property=A (profile measurement)+B; or
(ii) Surface or print property=C (profile measurement)+D (specular gloss, etc.)+E A, B, C, D, and E are values generated by the regression of the raw data. The values of A, B, C, D, and E will depend on the specific properties being measured. Some useful functions include the following.

$$\text{Print Surf} = A \text{ (average peak to valley height (Rtm))} + B$$

wherein A is a number from 0.32 to 0.42, preferably 0.37; and B is a number from $-0.29$ to $+0.05$, preferably $-0.12$.

$$\text{Sheet Gloss} = A \text{ (Pc} - \text{peaks/cm more than 2.5 micrometers above mean peak height)} + B$$

wherein A is a number from $-0.92$ to $-0.68$, preferably $-0.80$; and B is a number from 78.0 to 94.0, preferably 86.0.

$$\text{K and N percentage Ink Density Drop} = A \text{ (average peak to valley height)} + B$$

wherein A is a number from $-5.4$ to $-2.3$, preferably $-3.86$; and B is a number from 80.2 to 90.0, preferably 85.1.

$$\text{Print Gloss} = A \text{ (Pc} - \text{peaks/cm 2.5 micrometers above mean surface)} + B$$

wherein A is a number from $-0.54$ to $-0.26$, preferably $-0.40$; and B is a number from 90.1 to 98.0, preferably 94.1.

$$\text{Print Gloss} = C \text{ (Pc} - \text{peaks/cm 2.5 micrometers above mean surface)} + D \text{ (specular gloss 75°)} + E$$

wherein C is a number from $-0.60$ to $-0.20$, preferably $-0.40$; D is a number from 0.0 to $+0.28$, preferably $+0.09$; and E is a number from 82.0 to 89.9, preferably 85.9.

Having generated the correlation data it is a relatively simple matter to take several readings of the required profile parameter and where required one or more of specular gloss (preferably 75°), air resistance, and reflectance, from jumbo rolls in a paper mill and quickly get a fairly precise estimate of the potential print quality of the paper in that roll. In any test method it is important at least to consider the resolution reproducibility, and accuracy/precision of the test method. The resolution of the test method is high. The limiting factors are the geometry and dimension of the tip of the stylus. The preferred tip radius is in the 5 micrometer range. The tip will follow narrower contours, but will not register the full depth of such contours. With the current apparatus the resolution is $\pm 0.1$ micrometer. This is an extremely high resolution relative to the procedures which are currently used. The preproducibility of the test method is also high. Images which are superimposable may be obtained by drawing the stylus over the same area of paper. The accuracy and precision of the test is high, provided appropriate sampling techniques are used. For example, on measuring the contour at the corners and center of a $15'' \times 30''$ (38.1 cm $\times$ 76.2 cm) the standard deviation for the average surface above the mean was 0.1 micrometers.

EXAMPLES

The following examples are intended to illustrate, and not limit the invention.

Example 1

Samples of 20 enamel offset papers, graded #1 premium through #3 (e.g. #1 premium, #1, #2, #3), commercially available in the United States from a number of suppliers were obtained. The surface of each sample was characterized using profilometry. The profilometry was conducted using a Taylor-Hobson SURTRONIC 3P profilometer using a wide shoe pick up and cutoffs of 0.8 mm and 2.5 mm. The measurements taken were:
(i) mean deviation about a mean surface;
(ii) the average of 5 independent estimates of peak to valley height (Rtm);
(iii) the largest of Rtm (Ry)
(iv) the average of 5 independent estimates of the highest mean peak (Rpm);
(v) the percent of surface at a pre-selected depth below the highest peak (Tp—this is also called the bearing ratio); and
(vi) Pc—the number of peaks per cm which projected more than 2.5 micrometers above the mean peak height (Pc).

The papers were then tested for surface characterization of the paper using standard recognized (usually TAPPI) test methods. The tests were:
(i) Parker Surface Roughness (Print Surf);
(ii) Sheet Gloss;
(iii) K and N percentage Ink Density Drop (loss); and
(iv) Print Gloss.

Plots were made of the surface characterization by currently accepted techniques versus characterization by profilometry.

FIG. 1 is a plot of Parker Surface Roughness versus Rtm.

FIG. 2 is a plot of Sheet Gloss versus Peaks per cm 2.5 micrometers above mean surface.

FIG. 3 is a plot of K and N percentage Ink Density Drop versus Rtm.

FIG. 4 is a plot of print gloss versus Peaks per cm 2.5 micrometers above mean surface.

The correlation factor for the figures were also calculated and are indicated at the top of each figure. The correlation factors have high statistical significance for the number of samples used.

Example 2

A series of profile measurements and sheet gloss measurements were taken of 20 enamel offset paper samples. The actual print gloss of the paper was then measured. The measurements of actual print gloss, peak count of the unprinted paper (peaks per cm 2.5 micrometers above mean surface) and measured sheet gloss of the printed paper were statistically regressed to generate an equation for Print Gloss as a function of two variables (e.g. Print Gloss=85.9±4+(0.09±0.19)×Sheet Gloss−(0.40±0.20) Peak count (e.g. Dunfield equation)). The results are plotted in FIG. 5. At the top of the figure the correlation factor is given. The correlation 0.823 is very high.

Comparative Example

For demonstration purposes the 20 samples used in Example 1 were characterized for surface smoothness using the Sheffield air leak method. FIG. 6 is a plot of Parker Surface Roughness against Sheffield smoothness. The correlation factor is lower than for Example 2.

These examples show that surface profilometry is useful to predict print gloss characteristics of a paper with a high degree of certainty.

What is claimed is:

1. A rapid method to determine surface properties of coated paper, and one or more surface characterizations of the unprinted coated paper selected from the group consisting of specular gloss, reflectance and air resistance, and predict the printed properties of coated paper which comprises taking one or more measurements across the surface of an unprinted coated paper using a portable profilometer comprising a stylus, a traverse unit, a pick up, and one or more members selected from the group consisting of a recorder, a calculator, a display unit, and a computer interface means, wherein measurements are taken at cut offs of from 0.25 to 25 mm and the traverse has a stroke of from 1.5 to up to 25 mm to measure one or more parameters selected from the group consisting of mean surface contour, the average peak to valley height, the mean peak height, and the peak count per cm., in a direction perpendicular to the plane of the paper within the range +100 micrometers from the means surface of the paper, and relating the measured values to a calibration system selected from the group consisting of biaxial plots of the surface print properties of a representative sample of the papers against the measured values for the representative sample of at least nine papers; and surface properties and print properties of paper using a function generated by subjecting the surface properties, print properties and measured values of a representative sample of at least nine papers to a statistical regression to generate one or more functions of the formula:

(i) print or surface property of a paper=A (contour measurement)+B; and (ii) print or surface property of the paper=C (contour measurement)+D (measurement of a property of the unprinted paper selected from the group consisting of specular gloss, reflectance, and air resistance)+E; wherein A, B, C, D, and E are values generated by the statistical regression of the data.

2. A method according to claim 1 wherein the range of measurement of the surface contours of the paper in a direction perpendicular to the plane of the paper is within the limits ±10 microns.

3. A method according to claim 2 wherein the function is

Print Surf=A (average peak to valley height)+B wherein A is a number between 0.32 and 0.42; and B is a number between −0.29 and +0.05.

4. A method according to claim 2 wherein the function is

Sheet Gloss=A (Peak count−peaks per cm 2.5 microns above mean surface)+B wherein A is a number between −0.92 and −0.68; and B is a number between 78.0 and 94.0.

5. A method according to claim 2 wherein the function is

K and N percentage Ink Density Drop=A (average peak to valley height)+B wherein A is a number between −5.4 and −2.3; and B is a number between 80.2 and 90.0.

6. A method according to claim 2 wherein the function is

Print Gloss=A (Peak count−Peaks/cm 2.5 micrometers above mean surface)+B wherein A is a number between −0.54 and −0.26; and B is a number between 90.1 and 98.0.

7. A method according to claim 2 wherein the function is

Print Gloss=C (Peak count−peaks/cm 2.5 micrometers above mean surface)+D (75° Gloss)+E wherein C is a number between −0.60 and −0.29; D is a number between 0.0 and 0.28; and E is a number between 82.0 and 89.9.

* * * * *